(12) United States Patent
Ales et al.

(10) Patent No.: US 8,293,473 B2
(45) Date of Patent: Oct. 23, 2012

(54) ASSESSMENT OF REACTION KINETICS COMPATIBILITY BETWEEN POLYMERASE CHAIN REACTIONS

(75) Inventors: Tichopad Ales, Haar (DE); Bar Tzachi, Tivon (IL)

(73) Assignee: Labonnet Ltd., Ramat-Hasharon (IL)

( * ) Notice: Subject to any disclaimer, the term of this patent is extended or adjusted under 35 U.S.C. 154(b) by 387 days.

(21) Appl. No.: 12/294,392

(22) PCT Filed: Apr. 4, 2006

(86) PCT No.: PCT/IB2006/051025
§ 371 (c)(1),
(2), (4) Date: Sep. 24, 2008

(87) PCT Pub. No.: WO2007/113622
PCT Pub. Date: Oct. 11, 2007

(65) Prior Publication Data
US 2009/0176232 A1    Jul. 9, 2009

(51) Int. Cl.
*C12Q 1/68* (2006.01)
*C12P 19/34* (2006.01)

(52) U.S. Cl. ................ 435/6.12; 435/91.2

(58) Field of Classification Search .............. None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,455,175 A | 10/1995 | Wittwer et al. | |
| 6,303,305 B1 | 10/2001 | Wittwer et al. | |
| 7,013,237 B2 | 3/2006 | Endres | |
| 7,270,733 B2 | 9/2007 | Wikiel | |

FOREIGN PATENT DOCUMENTS

| | | |
|---|---|---|
| WO | WO 97/46707 | 12/1997 |
| WO | WO 97/46712 | 12/1997 |
| WO | WO 97/46714 | 12/1997 |

OTHER PUBLICATIONS

Bar et al. "Kinetic Outlier Detection (KOD) in real-time PCR." *Nucleic Acids Research*. vol. 31, No. 17 (2003), pp. 1-7.
Bar et al. "Kinetics quality assessment for relative quantification by real-time PCR." *BioTechniques*. vol. 29 (2005), pp. 333-340.
Chervoneva et al. "Statistical algorithm for assuring similar efficiency in standards and samples for absolute quantification by real-time reverse transcription polymerase chain reaction." *Analytical Biochemistry*. vol. 348 (2006), pp. 198-208.
Cook et al. "SAS programs for real-time RT-PCR having multiple independent samples." *BioTechniques*. vol. 37 (2004), pp. 990-995.
Garrett. "The chi-square plot: a tool for multivariate outlier recognition." *Journal of Geochemical Exploration*. vol. 32 (1989), pp. 319-341.
Gentle et al. "High-Resolution Semi-Quantitative Real-Time PCR without the Use of a Standard Curve." *BioTechniques*. vol. 31 (2001), pp. 502-508.
Higuchi et al. "Kinetic PCR Analysis: Real-time Monitoring of DNA Amplification Reactions." *Bio/Technology*. vol. 11(1993), pp. 1026-1030.
U.S. Appl. No. 60/696,127, filed Jun. 30, 2005, Woo et al.
Liu et al. "A New Quantitative Method of Real Time Reverse Transcription Polymerase Chain Reaction Assay Based on Simulation of Polymerase Chain Reaction Kinetics." *Analytical Biochemistry*. vol. 302 (2002), pp. 52-59.
Rousseeuw et al. "Unmasking Multivariate Outliers and Leverage Points." *Journal of the American Statistical Association*. vol. 85, No. 411 (1990), pp. 633-639.
Rutledge. "Sigmoidal curve-fitting redefines quantitative real-time PCR with the prospective of developing automated high-throughput applications." *Nucleic Acids Research*. vol. 32, No. 22 (2004), pp. 1-8.
Tichopad et al. "Improving quantitative real-time RT-PCR reproducibility by boosting primer-linked amplification efficiency." *Biotechnology Letters*. vol. 24 (2002), pp. 2053-2056.
Tichopad et al. "Inhibition of real-time RT-PCR quantification due to tissue-specific contaminants." *Molecular and Cellular Probes*. vol. 18 (2004), pp. 45-50.
Tichopad et al. "Model of inhibition of *Thermus aquaticus* polymerase and *Moloney murine leukemia virus* reverse transcriptase by tea polyphenols (+)-catechin and (−)-epigallocatechin-3-gallate." *Journal of Ethnopharmacology*. vol. 99 (2005), pp. 221-227.
Tichopad et al. "Standardized determination of real-time PCR efficiency from a single reaction set-up." *Nucleic Acids Research*. vol. 31, No. 20 (2003), pp. 1-6.
Wilhelm et al. "SoFAR: Software for Fully Automatic Evaluation of Real-Time PCR Data." *BioTechniques*. vol. 34, No. 2 (2003), pp. 324-332.
Wilhelm et al. "Validation of an algorithm for automatic quantification of nucleic acid copy numbers by real-time polymerase chain reaction." *Analytical Biochemistry*. vol. 317 (2003) pp. 218-225.
Zipper et al. "Investigations on DNA intercalation and surface binding by SYBR Green I, its structure determination and methodological implications." *Nucleic Acids Research*. vol. 32, No. 12 (2004), pp. 1-10.

*Primary Examiner* — Kenneth R. Horlick
*Assistant Examiner* — David Thomas
(74) *Attorney, Agent, or Firm* — Labonnet Ltd.

(57) ABSTRACT

A method compares amplification reaction kinetics between two or more quantitative polymerase chain reactions (PCR). These methods enable quality control and/or quality assessment for quantification of nucleic acids by PCR. The method estimates plurality of parameters from each reaction and compares them simultaneously between reactions.

14 Claims, 3 Drawing Sheets

ASSESSMENT OF REACTION KINETICS COMPATIBILITY BETWEEN POLYMERASE CHAIN REACTIONS

This application is a National Stage Application of PCT/IB2006/051025, filed Apr. 4, 2006, and which application is incorporated herein by reference. To the extent appropriate, a claim of priority is made to the above disclosed applications.

FIELD OF THE INVENTION

This invention applies to quantification of nucleic acid amount in samples by amplification of selected sequence of nucleotides in PCR with monitoring of amplification signal. Here the term 'sample' will consider the material from which nucleic acids are amplified. Quantification by PCR is based on non-linear amplification of selected sequence and its signal, whereas the reaction kinetics affects the result.

BACKGROUND OF THE INVENTION

Real-time quantitative PCR is a method to quantify selected polynucleotide sequence by amplifying its initial concentration until well detectable level. The PCR reaction itself is almost an obligatory tool in every molecular biological laboratory and the principle behind this method was described in U.S. Pat. No. 4,683,195 (Mullis et al.) and U.S. Pat. No. 4,683,202 (Mullis). Real-time quantitative PCR induces amplification of nucleic acid amount in sample. This amplification is strongly non-linear and for simplification considered as exponential in its most progressive phase. The amplification of selected locus of DNA is achieved by repeated cycles of set temperature program that facilitates DNA replication by polymerase enzyme. The locus to be amplified is delimited by pair of primers that anneal to the template by molecular affinity and facilitate polymerization of new strand of DNA from supplied essential nucleotides by polymerase enzyme. Eventually, the finalized double stranded DNA product melts into two single stranded molecules by elevated temperature. To clearly separate and facilitates each of these fundamental steps, temperature regime is controlled and repeated in every cycle by the PCR thermal cycler. A recent embodiment of a thermal cycler is described in U.S. Pat. No. 5,455,175 (Wittwer et al.). The fundamental improvement from a qualitative towards quantitative method was facilitated by addition of fluorescence emitting agent into reaction mix whose fluorescence emission can be monitored throughout the reaction progress. Added into reaction, fluorescence emitting agent closely reflects the current concentration of the nucleic acid mass formed cycle by cycle by interacting with it (Higuchi et al., 1993). In this way, a trackable reaction kinetics trajectory is generated having a specific geometry. The signal emitted by interaction of signaling agent with reaction product is monitored once per cycle and when strengthened enough, the cycle number or its fraction is recorded at this threshold. In this way the so called threshold cycle (Ct) is obtained. To say when the threshold signal of an individual PCR has been reached, qualified arbitrary decision is made or a computing procedure is employed. Examples of such techniques are detailed in U.S. Pat. No. 6,303,305 (Wittwer et al.), WO 97/46707, WO 97/46712 and WO 97/46714 (Wittwer et al.).

Kinetics Compatibility

The herein claimed invention provide improvement to the verification of amplification kinetics compatibility between PCRs published by Bar et al. (2003, 2005) and Chervoneva et al (2006). The underlying concept of this method is based on the fact that any unwanted erroneous effect will primarily affect the amplification reaction kinetics visualized by the specific geometry of each PCR kinetics trajectory and only secondarily the amount of analyte calculated. Therefore, compatible amplification kinetics between PCRs to be compared is the elementary prerequisite of reliable results. The herein presented invention provides a method to achieve such comparison by comparing the PCR kinetics trajectories of the PCRs performed under investigations by analyzing their geometry and applying suitable metrics to facilitate statistical inference about similarity or heterogeneity of the compared trajectories. Only PCRs with comparable PCR kinetics trajectories can be considered compatible and hence suitable for quantitative determination of a DNA analyte.

Characterization of Amplification Kinetics

The amplification kinetics can be visualized by two-dimensional plot of signal measurements versus PCR cycle number. The full plot of all signal readings has sigmoid character, provided data from enough cycles are plotted. As discussed above, this is called the PCR kinetics trajectory.

Figure 1:
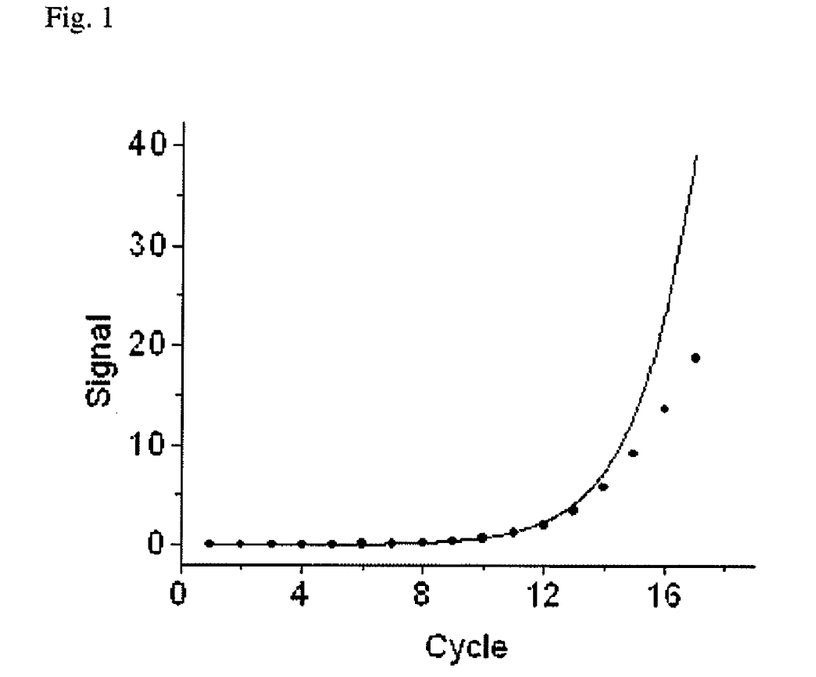
FIG. 1: Exponential model of the amplification, obtained by smoothing cycles 8 to 11, versus real amplification data.

Traditional approach to the PCR says that the PCR is a chain reaction progressing in a fashion close to perfect doubling. That is, every selected DNA molecule in reaction becomes a target template for synthesis of its one new complementary copy within one cycle of the polymerase reaction. Such an ideal doubling fashion of the PCR reaction can be described by the following model:

$$P = T \cdot (1 + E^n); E \rightarrow 1 \qquad [1]$$

where P is the PCR product measured after n cycles, T is the starting amount of the target sequence, E is the amplification efficiency expressed as the proportion of target molecules copied in PCR cycle (from 0, representing no amplification, to 1, representing the ideal doubling). Description of the reaction kinetics by the exponential models can be, however, considered as a simplification of the true nature of the reaction (Rutledge 2004). In fact, no non-discrete section of the reaction trajectory behaves really exponentially and with every cycle the efficiency declines (FIG. 1).

Figure 2:
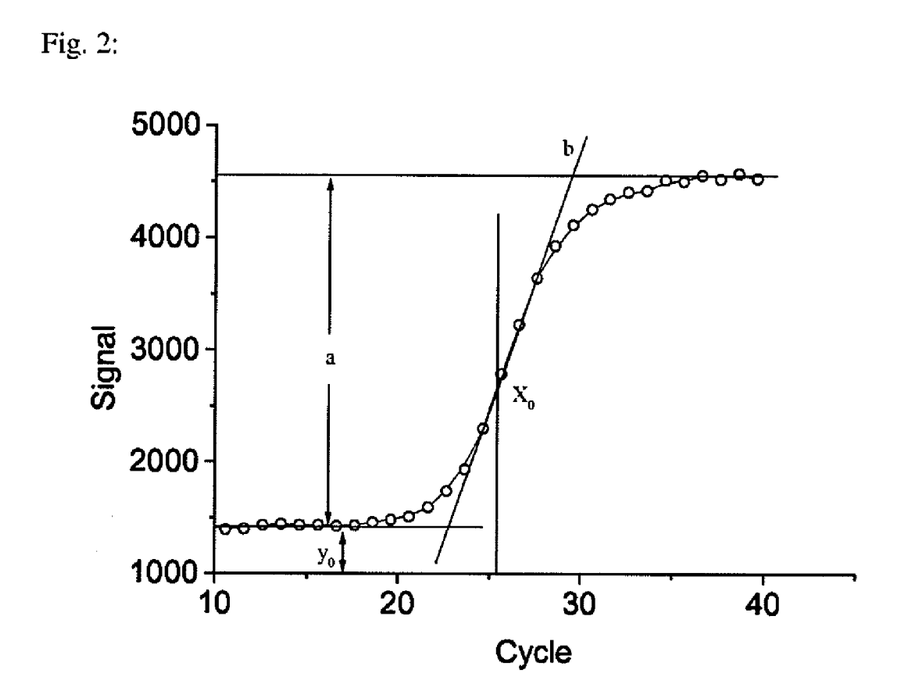
FIG. 2: Four-parametric sigmoid model.

Several methods have been published describing methods of computing the amplification efficiency from the portion of the signal trajectory considered close to exponential. This portion was usually selected somewhere between the departure from the background phase and the entry into the plateau phase and consisted of some three to ten signal readings (Bar et al. 2003, Tichopad et al. 2003). Alternatively, selected portion was transformed by log of the signal values and fitted by linear model (Liu and Saint, 2002). This approach is, however, based on the same assumption of exponential amplification data which, after log transformation, become linear. In addition, selection of the portion to be fitted by the exponential model is done more or less arbitrarily and any shift down- or upwards affects the amplification efficiency calculated. What makes PCR kinetics even more complex is the interaction between the signal agent and the product formed. It was shown that this does not remain constant but rather changes with the reaction progress (Zipperet et al. 2004). Herein presented invention utilizes recent disclosures about the more complex amplification kinetics. With each cycle the efficiency decreases until it ceases completely in the plateau phase. Hence, the efficiency E from Equation 1 is instable and cycle-dependent. This largely invalidates its use alone as a metrics for reliable and robust geometric characterizing each PCR kinetics trajectory. The amplification kinetics can theoretically be broken down into two components, the growth component and the saturation component. Both components are present already in the first cycle, usually strongly in favor of the growth component. As the reaction progresses, the balance changes until the saturation component dominates over the growth. Such dynamics can be described by a model including more than one parameter of the kinetics. A good example is fitting the entire set of data by the following model (Tichopad et al., 2002), where the plateau height is the measure of saturation:

$$f(x) = y_0 + \frac{a}{1 + e^{-(x-x0)/b}} \quad [2]$$

The f(x) is the value of the function computed at cycle x, $y_0$ is the background fluorescence, a is the difference between maximal and background fluorescence, e is the natural logarithm base, x0 is the x-coordinate of the inflexion point of the amplification curve, and b is a parameter reflecting the slope of the curve (FIG. 2).

The parameter a can be related to the saturation components whereas the parameter b is more strongly related to the growth component. If both taken simultaneously for characterization of the reaction kinetics, they add together more information about the amplification kinetics than each of them separately. Moreover, the parameters are not fully independent, in fact they are correlated. The direction and strength of the correlation is another contribution to the unique characterization of the kinetics.

Another multi-parametric characterization of the amplification kinetics can be reached by estimation of the amplification kinetics in several discrete points of the trajectory. Derived from equation [2], reaction-specific efficiency can be estimated from the predicted values f(x) at any cycle x by Equation [6]:

$$E(x) = \frac{f(x+1) - y_0}{f(x) - y_0} - 1 \quad [3]$$

In this way, several parameters describing the amplification kinetics at different cycles along the trajectory can be obtained. Relying on only one efficiency estimate (e.g. at cycle 10) would provide only insufficient information about the entire reaction kinetics. Neither here the consecutive estimates of efficiency are fully independent, providing thus additional information via the strength and direction of the correlation.

Characterization of Kinetics by Covariance Matrix

The straightforward method to compare similarity of one kinetics parameter, is to log transform the data points in the exponential phase and test the similarity of the slopes of two curves by t-test (Payton 2004) or Zar's method (Gentle 2001). However, the relatively late stage the first clear signal is detected above the noise, and the smooth change of efficiency along the PCR causes to a difficulty in estimating the efficiency of compared PCRs exactly at the same phase of the reaction. Therefore, verification of compatibility based on parameters from plurality of reactions must be obtained. In such statistical design, the shape and size of multivariate data are described by the covariance matrix, a fundamental term in the linear algebra and multivariate statistics. It is a matrix of covariances between elements of vectors X an Y that represent here the kinetics parameters $x_i$ and $y_i$ for several reactions. Intuitively, covariance is the measure of how much two variables vary together. That is to say, the covariance becomes more positive for each pair of values which differ from their mean in the same direction, and becomes more negative with each pair of values which differ from their mean in opposite directions. In this way, the more often they differ in the same direction, the more positive the covariance, and the more often they differ in opposite directions, the more negative the covariance.

Utilized Disclosures

Bar et all (2003, 2005) and Chervoneva et al (2006) reported on methods of kinetics outlier detection among group of PCRs, employing defined reference set. In both methods, signal readings in the most progressive parts of the amplification trajectory were fitted with the exponential model and efficiency of the assumed exponential amplification was figured out. Subsequently, individual PCRs were compared statistically with defined reference and PCRs with significantly outlying efficiency values were recommended for exclusion. Both methods, in despite of their designation, in fact ignored the kinetics of the amplification, which is characterized by substantial decay of the amplification efficiency with every cycle, an assumed rather constant efficiency in the fitted region. The major shortcoming of these methods is that selecting a particular data points along the trajectory for the exponential fit affects the efficiency obtained, and thus the resolution between different PCRs.

Tichopad et al employed the four parametric sigmoid model (Equation [2]) to describe and compare amplification performances on different reaction substrate manipulated by primer selection (2002), different extraction residua (2004) and added inhibitor (2005). In this way, conclusion could have been drown from the experimental set-up on an effect of minute reaction disturbance on the reaction performance. The comparison of reaction was performed by means of statistical tests that compared individual parameters obtained from the fitted model one by one between groups of PCRs. This approach might show an effect of minute contaminations among reaction set-ups on the steepness of the reaction trajectory as described by the parameter b (FIG. 2) or on the height of the amplification curve as described by parameter a. Such approach provided user with the possibility to validate comparability of groups of PCRs where heterogeneous reaction conditions are assumed. This however was not within the focus of the cited works. The focus rather was only to show that there is an effect of added compounds (Tichopad 2004, 2005) or residua (2004) on the kinetics. Interestingly, both indicators of performance a and b were distinctly affected by the contaminants and not always alleged the same conclusion. Considering this, drawing conclusion on kinetics heterogeneity among PCRs could be impossible where conflicting outcomes from both parameters would be obtained. For this reason, comparison based on a single parameter might not be suited to draw numerically supported decision on compatibility among PCRs.

Quantification of nucleic acid in sample from obtained maximum of defined derivative of smoothed signal readings is described in U.S. Pat. No. 6,303,305 (Wittwer et al., 2001). The said invention is based on assumed relation between the geometric shape of the amplification curve, as characterized by the maximum of, for instance, second derivative, and the initial amount of nucleic acid. In herein claimed invention the plurality of n-th derivative maxima is used not to quantify nucleic acid amount, but to facilitate comparison of amplification curves between reactions.

DETAILED DESCRIPTION

It is within the scope of herein claimed invention to provide a method for detecting individual PCRs with amplification kinetics significantly different from the plurality of reactions.

It is also within the scope of herein claimed invention to provide a method for validating comparability between two ore more groups of PCRs.

For the purpose of herein claimed invention, full or partial PCR amplification trajectory can be described by fitting signal readings with a suitable model with more than one parameter. In general, the more parameters such model contains, the better flexibility of the fit. For the purpose of herein claimed invention it is peripheral, whether the model used describes mechanistically all underlying molecular processes or it just traces the trajectory as to its geometry.

The amplification kinetics as reported by the signal readings is an outgrowth of dynamic molecular processes and changes in their rate. These changes can reach unknown n-th order. Therefore, for the purpose of herein claimed invention the amplification kinetics is a multi-parametric measure. It is out of scope of the herein claimed invention to determine all underlying processes in order to compare reactions.

Determining and adding into statistical analysis further parameter/s contributing to description of the amplification kinetics is considered within the scope of herein claimed invention as long as the new parameter is not fully dependent on some already used parameter. It is not within the scope of the herein claimed invention to determine a minimal number of parameters necessary for minimal adequate description of the amplification kinetics as long as there are at least two of them. Such parameters can be drawn directly from a model fitted on the primary signal reading data. They can also be drawn form a model fitted to a derived secondary data obtained by calculating the maximum of the first, second or generally n-th order derivative. It is still within the scope of the herein invention, when at least one parameter is the value of the first, second or generally n-th order derivative in a defined point of the amplification trajectory.

It is considered the principal improvement to all recent methods of comparing PCR amplifications, to compare plurality of parameters simultaneously, based on their covariance matrix. This approach is an upgrade to all methods, where parameters from smoothing model were compared one-by one, occasionally yielding conflicting outcomes. To facilitate multi-parametric comparison, multivariate statistical test must be employed operating with a single overall probability. It is also important, that each contributing parameter is at lest minimally independent from any other parameter used for the characterization of kinetics.

Multivariate Outlier Detection

It is within the scope of herein claimed invention to test whether individual kinetics is significantly distant from defined reference. The shape and size of multivariate data are quantified by the covariance matrix. The basis for the multivariate outlier detection which takes into account the covariance matrix is the Mahalanobis distance (Mahalanobis, 1936). It differs from Euclidean distance in that it takes into account the correlations of the data set. For a p-dimensional multivariate PCR xi (i=1; : : : ; n) the Mahalanobis distance is defined as $$MDi = ((x_i - t)^T C^{-1}(x_i - t))^{1/2} \text{ for } i=1, \ldots, n$$

where t is the estimated multivariate location and C the estimated covariance matrix. Usually, t is the multivariate arithmetic mean, and C is the PCR covariance matrix. For multivariate normally distributed data the values are approximately chi-square distributed with p degrees of freedom (chi-square$_p$). Multivariate outliers can now simply be defined as observations having a large (squared) Mahalanobis distance (dsq). For this purpose, a quantile of the chi-squared distribution (e.g., the 97.5% quantile) could be considered. The Mahalanobis distances need to be estimated by a robust procedure in order to provide reliable measures for the recognition of outliers. Single extreme observations, or groups of observations, departing from the main data structure can have a severe influence to this distance measure, because both location and covariance are usually estimated in a non-robust manner. Many robust estimators for location and covariance have been introduced in the literature. The minimum covariance determinant (MCD) estimator is probably most frequently used in practice, partly because a computationally fast algorithm is available (Rousseeuw and Van Driessen, 1999). Using robust estimators of location and scatter in formula (I) leads to so-called robust distances (RD). Rousseeuw and Van Zomeren (1990) used these RDs for multivariate outlier detection. If the squared RD for an observation is larger than, say, chi-square$_{p=0.975}$, it can be declared a candidate outlier. This approach, however has shortcomings: It does not account for the sample size n of the data, and, independently from the data structure, observations could be flagged as outliers even it they belong to the data distribution. A better procedure than using a fixed threshold is to adjust the threshold to the data set at hand. Garrett (1989) used the chi-square plot for this purpose, by plotting the squared Mahalanobis distances (which have to be computed at the basis of robust estimations of location and scatter) against the quantiles of chi-square$_p$, the most extreme points are deleted until the remaining points follow a straight line. The deleted points are the identified outliers. Procedures that do not require analyst intervention were also published.

EXAMPLE 1

Amplification of Rat 18S Locus in Excess of dNTP. Kinetics Description Based on First and Second Order Parameters To test resolution abilities of selected parameters, 15 PCR runs were performed with samples containing serially diluted stock DNA. The stock DNA was obtained as a purified product of previous PCR on selected locus of 18S rat gene. In addition, further 11 replicates of the stock DNA were prepared and contaminated with step-wise elevated concentrations of 0.1-1 mM dNTP, so that, eventually, excess of dNTP over the recommended concentration was obtained in each of the eleven test PCRs. This experimental set-up was chosen to demonstrate a mistake done by labor worker, pipetting more than once into the same sample.

The 15 PCRs from the uncontaminated samples were considered reference set whereas the eleven PCRs from the manipulated samples were investigated on their compatibility with the reference set.

Figure 3:
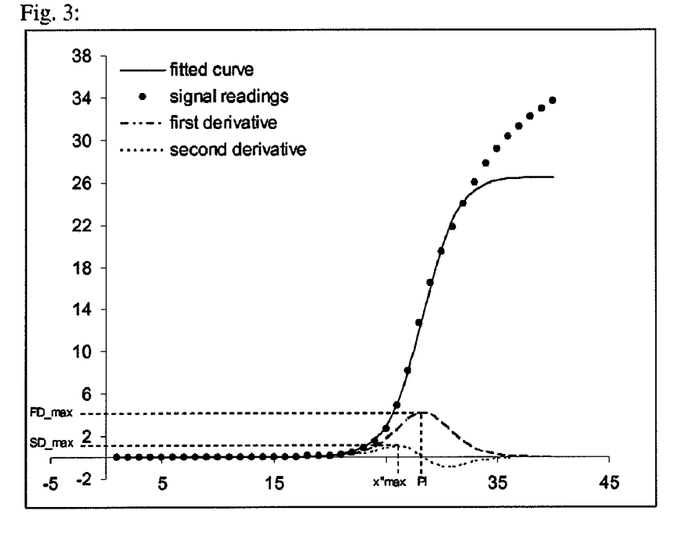
FIG. 3: Plot of data fitted by smoothing model up to the $4^{th}$ point above the point of inflection. The first and the second derivative of the model are calculated

Model (4) was fitted over the fluorescence readings up to the $5^{th}$ reading above the point of inflexion of the time series. Further data points above the $5^{th}$ reading were excluded from the fit to prevent the plateau to affect the fit. The parameters chosen for the outlier detection were the value of the first derivative maximum (FD_max) and value of the second derivative maximum (FD_max) calculated from the model parameters. The FD_max was obtained by calculating the value of the equation of second order for the fractional number of cycles at the point of inflection (PI). The SD_max was obtained by calculating first the fractional number of cycles at the maximal second derivative (x"max). This was obtained by resolving the equation of the third order set equal to zero, f" (x)=0, for the x"max. As soon as the x"max could be figured out, the SD_max was calculated from the equation of second order for the x"max (FIG. 3).

The parameters FD_max and SD_max were taken to calculate the Mahalanobis distance according to formula 5 and its probability based on chi-square distribution. A reaction with dsq value with probability below 0.05 were considered outliers and received the weight 0.

| Name | weight | dsq | prob | FD_x0 | SD_pos |
|---|---|---|---|---|---|
| Ref_25a | 1 | 0.500 | 0.77889 | 4.42192 | 1.05777 |
| Ref_1c | 1 | 0.774 | 0.67923 | 4.47612 | 1.07777 |
| Ref_125b | 1 | 0.809 | 0.66720 | 4.25978 | 1.03143 |
| Ref_5c | 1 | 0.945 | 0.62341 | 4.32504 | 1.05100 |
| Ref_1a | 1 | 1.320 | 0.51698 | 4.16313 | 1.00492 |
| Ref_25c | 1 | 1.520 | 0.46766 | 4.53579 | 1.08982 |
| Ref_125a | 1 | 1.622 | 0.44444 | 4.55325 | 1.09963 |
| Ref_1b | 1 | 1.713 | 0.42474 | 4.55810 | 1.10366 |
| Ref_125c | 1 | 1.725 | 0.42204 | 4.16191 | 1.00759 |
| Ref_5a | 1 | 2.175 | 0.33699 | 4.11974 | 0.99647 |
| Ref_625a | 1 | 2.283 | 0.31937 | 4.16770 | 0.97266 |
| Ref_625c | 1 | 3.932 | 0.14001 | 4.28508 | 0.99559 |
| Ref_625b | 1 | 4.683 | 0.09620 | 3.93218 | 0.91201 |
| Ref_25b | 0 | 15.676 | 0.00039 | 4.97769 | 1.18841 |
| Ref_5b | 0 | 24.661 | 0.00000 | 3.80990 | 0.82921 |
| Test_001 | 0 | 32.744 | 0.00000 | 4.17516 | 0.90939 |
| Test_002 | 0 | 34.466 | 0.00000 | 4.18135 | 0.90881 |
| Test_007 | 0 | 37.923 | 0.00000 | 4.98383 | 1.14299 |
| Test_005 | 0 | 39.122 | 0.00000 | 5.13415 | 1.19212 |
| Test_004 | 0 | 42.784 | 0.00000 | 4.88878 | 1.10555 |
| Test_006 | 0 | 56.612 | 0.00000 | 4.91579 | 1.09763 |
| Test_008 | 0 | 69.247 | 0.00000 | 4.38002 | 0.92674 |
| Test_003 | 0 | 87.593 | 0.00000 | 3.71850 | 0.73475 |
| Test_009 | 0 | 97.802 | 0.00000 | 3.95150 | 0.78655 |
| Test_011 | 0 | 132.673 | 0.00000 | 3.88868 | 0.74509 |
| Test_010 | 0 | 148.110 | 0.00000 | 3.53477 | 0.64390 |

Result

Together with all samples with excess of dNTP two reference samples Ref_25b and Ref_5b were excluded from the initial reference set as they were diagnosed as outliers. This is due to fact that the test is repeated several times to assure robustness by first excluding possible outliers from the reference set, producing the final valid reference set with a minimal justified spread.

Figure 4:
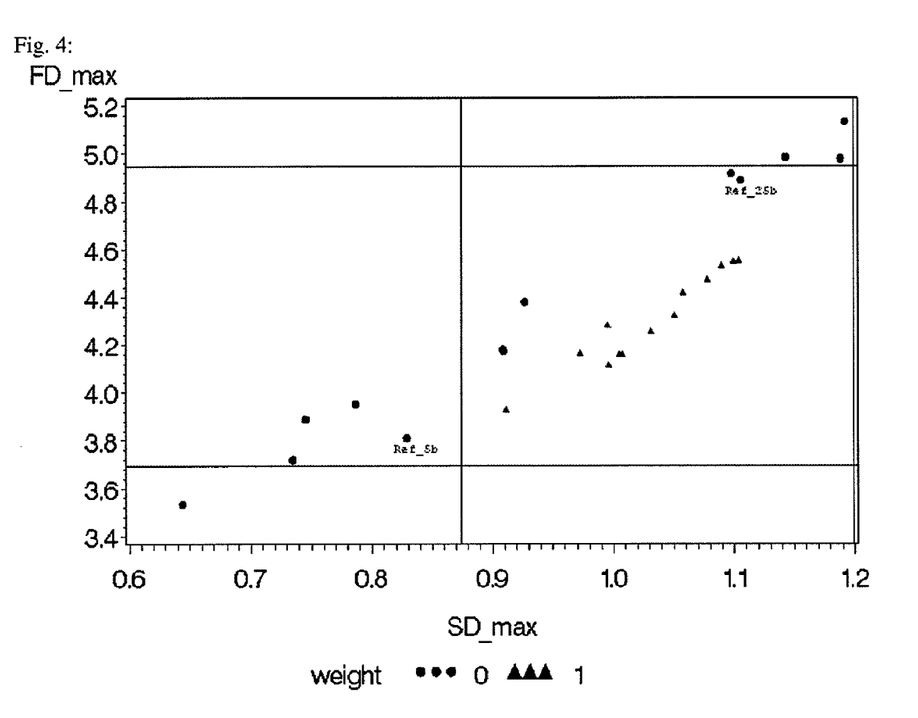
FIG. 4: Two dimensional plot of test PCRs (points) versus reference set (triangles), whereas two PCRs (flagged points) were excluded from the initial reference set and did not contribute to the final reference set. The inner lines define traditional boundaries for outliers for each of the two parameters. The boundaries were obtained as upper quartile plus 1.5 times interquartile range and lower quartile minus 1.5 times interquartile range.

FIG. 4 shows that the resolution improves drastically when two parameters are taken simultaneously instead of each one separately. The inner lines define the boundaries of extreme values. If only the SD_max was taken for a quality control, 7 out of 11 samples with aberrant PCR would pass, in case of SD_max it would be 6 samples with aberrant PCR.

EXAMPLE 2

Amplification of Rat 18S Locus in Excess of dNTP. Kinetics Description Based on Model Parameters The same experimental set-up as in Example 1 was applied. Four parameters a and b were obtained from the fitted model. This parameters were taken to calculate the Mahalanobis distance according to formula 5 and its probability based on chi-square distribution. Outlier was defined as a PCR with dsq value with probability below 0.05.

| Name | weight | dsq | prob | a | b |
|---|---|---|---|---|---|
| Ref_25a | 1 | 0.484 | 0.78511 | 28.4602 | 1.6090 |
| Ref_1c | 1 | 0.769 | 0.68068 | 28.6211 | 1.5985 |
| Ref_125b | 1 | 0.813 | 0.66587 | 27.0859 | 1.5896 |
| Ref_5c | 1 | 0.894 | 0.63965 | 27.4021 | 1.5839 |
| Ref_1a | 1 | 1.358 | 0.50721 | 26.5533 | 1.5946 |

-continued

| Name | weight | dsq | prob | a | b |
|---|---|---|---|---|---|
| Ref_25c | 1 | 1.515 | 0.46893 | 29.0641 | 1.6019 |
| Ref_125a | 1 | 1.596 | 0.45014 | 29.0272 | 1.5938 |
| Ref_1b | 1 | 1.657 | 0.43671 | 28.9829 | 1.5896 |
| Ref_125c | 1 | 1.760 | 0.41479 | 26.4674 | 1.5899 |
| Ref_625a | 1 | 2.216 | 0.33014 | 27.4942 | 1.6492 |
| Ref_5a | 1 | 2.225 | 0.32871 | 26.2231 | 1.5913 |
| Ref_625c | 1 | 3.724 | 0.15538 | 28.3951 | 1.6566 |
| Ref_625b | 1 | 4.989 | 0.08255 | 26.1021 | 1.6595 |
| Ref_25b | 0 | 15.605 | 0.00041 | 32.0994 | 1.6122 |
| Ref_5b | 0 | 33.888 | 0.00000 | 26.9509 | 1.7685 |
| Test_0.07 | 0 | 35.444 | 0.00000 | 33.4574 | 1.6783 |
| Test_0.05 | 0 | 37.258 | 0.00000 | 34.0429 | 1.6577 |
| Test_0.01 | 0 | 38.025 | 0.00000 | 29.5125 | 1.7671 |
| Test_0.04 | 0 | 39.789 | 0.00000 | 33.2837 | 1.7020 |
| Test_0.02 | 0 | 40.096 | 0.00000 | 29.6190 | 1.7709 |
| Test_0.06 | 0 | 52.752 | 0.00000 | 33.8954 | 1.7238 |
| Test_0.08 | 0 | 78.475 | 0.00000 | 31.8714 | 1.8191 |
| Test_0.09 | 0 | 153.257 | 0.00000 | 30.5637 | 1.9337 |
| Test_0.03 | 0 | 157.594 | 0.00000 | 28.9736 | 1.9479 |
| Test_0.11 | 0 | 232.346 | 0.00000 | 31.2466 | 2.0088 |
| Test_0.10 | 0 | 349.649 | 0.00000 | 29.8752 | 2.1130 |

Result

Figure 5:
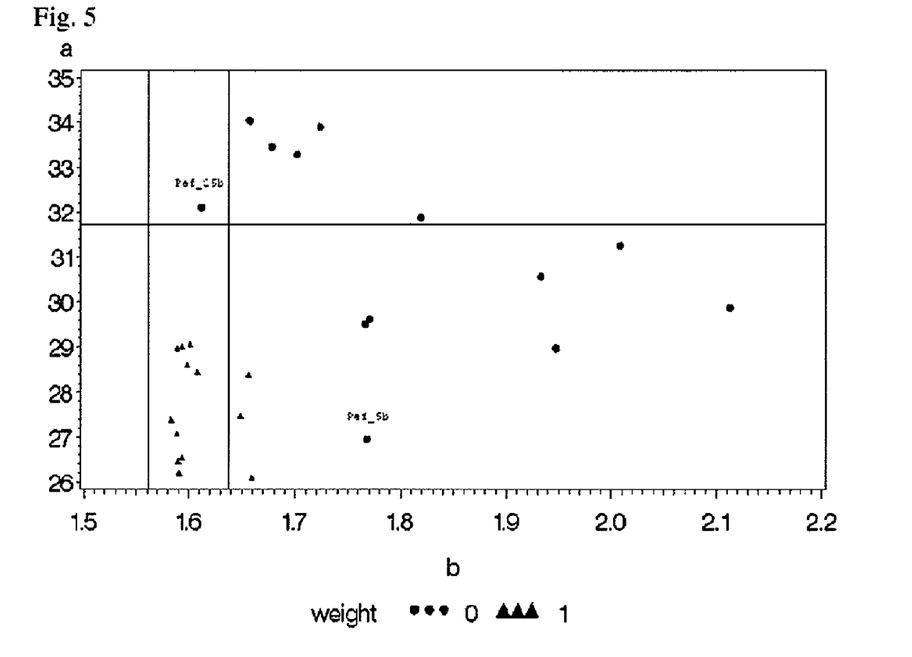
FIG. 5. Two-dimensional plot of resulting outliers (points). PCRs with weight 1 (triangles) remained after 4 passes in the reference set. Except of two excluded reference PCRs (flagged points) all reference PCRs (triangles) show distinct two-dimensional location separated well from the test PCRs. The inner vertical and horizontal lines present boundaries of extreme values calculated for the reduced reference set.

The table above shows a distinct trend to exclude samples with the highest dNTP concentrations, for example Test_0.10 with dsq 349.649 and Test 0.11 with dsq 232.346. FIG. 5 shows that only the multivariate approach has strong enough resolution to well separate reference PCRs from the manipulated test PCRs.

Multivariate Group Comparison

It is within the scope of herein claimed invention to test homogeneity between groups of PCRs by comparing their kinetics parameters. Since the kinetics is described by more than one parameter, multivariate approach must be employed. Multiple Analysis of Variance (MANOVA) is an extension of analysis of variance (ANOVA). MANOVA is the technique used for assessing group differences across multiple metric dependent variables simultaneously. MANOVA is used, where more than one dependant variable are under control of one or more independent variables, to determine the effect of the independent variable/s on the dependant variables. MANOVA is useful in experimental situations where at least some of the independent variables are manipulated.

The major reason why MANOVA is superior to repeated use of ANOVA on each parameter is that MANOVA can protect against Type I errors that might occur if multiple ANOVA's were conducted independently on each kinetics parameter. Repeated univariate measures can dramatically increase Type I error (rejecting a true null hypothesis). And, multiple univariate measures do not equal a multivariate measure because they do not take into account colinearity (correlations among dependent variables). If the dependent variables were uncorrelated with each other, it may be that a series of univariate ANOVA tests would be acceptable, provided some correction for the overall probability (e.g. Bonferroni correction) would be adopted. Since the kinetics parameters are correlated most of the time, MANOVA is superior. This is because ANOVA only tests differences in means, whereas MANOVA is sensitive not only to mean differences but also to the direction and size of correlations among the parameters. MANOVA will test groups to differ if they differ in correlation among the parameters even though their means are the same on the parameters, whereas ANOVA will fail to reject the null hypotheses of no group differences. MANOVA acts as an inherent Bonferroni correction (CITATION) by keeping the experiment-wide probability of making Type I error less than 5%. MANOVA uses multivariate F values such as Wilks' lambda (CITATION), Hotelling's trace (CITATION) and Pillai's criterion (CITATION).

EXAMPLE 3

Amplification of Selected Locus of Ubiquitin Gene in Bovine Liver after Different Duration of Storage DNA extracted from bovine liver was stored in −20 Grad Celsius for time period of 1) one day and 2) one week. Herein it was tested, whether different integrity of samples has also an effect on the amplification performance. Where heterogeneous amplification kinetics is found, any result drawn from comparison of the two groups must be taken with caution.
Result 1:
Result based on repeated use of one-way ANOVA model on each parameter SD_max and FD_max with no correction for overall probability.

| Source | DF | Sum of Squares | Mean Square | F Value | Pr > F |
|---|---|---|---|---|---|
| a) Result of ANOVA on FD_max | | | | | |
| Model | 1 | 0.05 | 0.05 | 0.13 | 0.73 |
| Error | 10 | 4.25 | 0.42 | | |
| Corrected Total | 11 | 4.31 | | | |
| b) Result of ANOVA on SD_max | | | | | |
| Model | 1 | 0.05 | 0.05 | 1.44 | 0.26 |
| Error | 10 | 0.34 | 0.03 | | |
| Corrected Total | 11 | 0.39 | | | |

Examining either the FD_max (p=0.73) or the SD_max (p=0.26), no significant difference in amplification kinetics was found by the ANOVA test between the two groups. Having the Bonferroni-corrected overall probability alpha=0.025 for two tests, the obtained probability values 0.73 and 0.26 are still far from indicating significant difference between groups. However, since the _max and SD_max are correlated (Pearson correlation coefficient=0.96) the correlation must be taken into account when correcting for the overall probability, producing for each test the alpha=0.0485. Neither here any significant difference between groups is detected.
Result 2:
Result based on simultaneous test of both parameters SD_max and FD_max within the MANOVA model.

| MANOVA Test Criteria and Exact F Statistics for the Hypothesis of No Overall Storage Effect H = Type III SSCP Matrix for storage E = Error SSCP Matrix S = 1 M = 0 N = 3.5 | | | | | |
|---|---|---|---|---|---|
| Statistic | Value | F Value | Num DF | Den DF | Pr > F |
| Wilks' Lambda | 0.28 | 11.63 | 2 | 9 | 0.003 |
| Pillai's Trace | 0.72 | 11.63 | 2 | 9 | 0.003 |
| Hotelling-Lawley Trace | 2.58 | 11.63 | 2 | 9 | 0.003 |
| Roy's Greatest Root | 2.58 | 11.63 | 2 | 9 | 0.003 |

Figure 6:
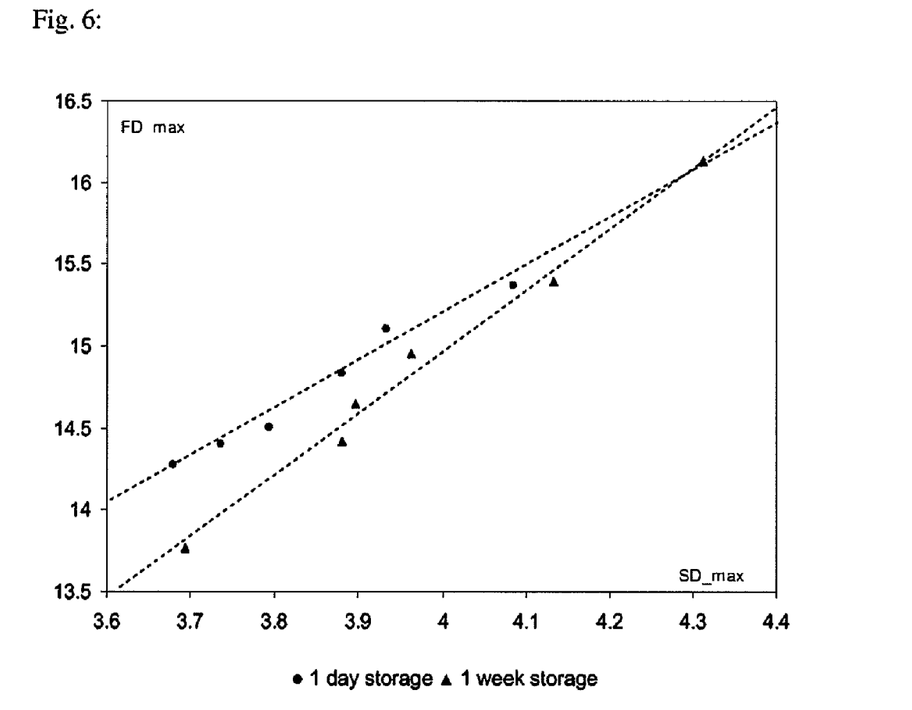
FIG. 6: Difference in location and direction of correlation of the kinetics parameters in two groups of PCRs with varying storage time.

Using all four tests, a highly significant (p=0.003) difference between groups could be detected. This shows that the multivariate approach only can sensitively enough detect group difference in amplification kinetics where this is assumed. FIG. 6 shows that the difference between the two groups of PCRs can be disclosed only by the multi-parametric data. Considering location of either the SD_max on the x axis or the FD_max on the y axis, no manifest difference in means appears. Instead, the correlation between the parameters within each group introduces the heterogeneity considered while calculating the MANOVA model. Regression lines are plotted in FIG. 6 to show different directions of the correlations.

REFERENCES

U.S. Patent References

U.S. Pat. No. 4,683,195 July 1987 Mullis et al.
U.S. Pat. No. 4,683,202 July 1987 Mullis et al.
U.S. Pat. No. 5,455,175 October 1995 Wittwer et al.
U.S. Pat. No. 6,303,305 October 2001 Wittwer et al.

Foreign Patent References

WO 97/46707 December 1997 WO
WO 97/46712 December 1997 WO
WO 97/46714 December 1997 WO
Bar, T., Ståhlberg, A., Muszta, A. and Kubista, M. (2003) *Nucleic Acids Res*, 31, E105.
Bar, T. and Muszta, A. (2005) *Biotechniques*, 39, 333-334, 336, 338 passim.
Gentle, A., Anastasopoulos, F. and McBrien, N. A. (2001) *Biotechniques*, 31, 502, 504-506, 508
Higuchi, R., Fockler, C., Dollinger, G. and Watson, R. (1993) *Biotechnology* (N Y), 11, 1026-1030.
Liu W, S. D. (2002) *Analytical Biochemistry*, 302, 52-59.
Mahalanobis, P. C. (1936): *Proceedings of the national Institute of Science, India* Vol. 12 pp. 49-55
Peyton Cook, C. F., Morgen Hickey, Eun-Soo Han, and Kenton S. Miller. (2004) *BioTechinques*, 37, 990-995.
Rousseeuw P. J., Van Driessen K. (1999). *Technometrics. Vol.* 41, pp. 212-223.

Rousseeuw P. J., Van Zomeren B. C. (1990). *Journal of the American Statistical Association. Vol.* 85(411), pp. 633-651.

Tichopad, A., Dilger, M., Schwarz, G. and Pfaffl, M. W. (2003) *Nucleic Acids Res,* 31, e122.

Zipper, H., Brunner, H., Bernhagen, J. and Vitzthum, F. (2004) *Nucleic Acids Res,* 32, e103.

What is claimed is:

1. A method for the assessment of compatibility of an individual PCR with a defined reference of PCRs comprising the steps of:
    a) amplifying by PCR a nucleic acid together with a signaling agent in an investigated sample;
    b) obtaining a reference set by amplifying by PCR a plurality of samples with a reference nucleic acid sequence together with a signaling agent;
    c) obtaining a time series of signals from every PCR by reading and storing at a plurality of time points at least one signal whose intensity is related to the quantity of the nucleic acid sequence formed in the PCR;
    d) from the time series of signals of every PCR, deriving a plurality of parameters characterizing change of the signal accompanying the reaction progression;
    e) simultaneously comparing by a single statistical test the parameters of the investigated PCR with the parameters of the PCRs of the reference set;
    f) based on the probability obtained from the statistical test, drawing an inference on the geometry of the reaction kinetics of the investigated PCR with the reference set, wherein a parallel geometry indicates reaction kinetics compatible between the investigated PCR and the reference set; and
    g) informing a user about one or more PCRs with non-parallel geometry if this is elicited in step f.

2. A method for the assessment of compatibility of individual amplification of a nucleic acid sequence with a defined reference nucleic acid sequence comprising the steps of:
    a) amplifying by PCR the nucleic acid together with a signaling agent in a sample;
    b) obtaining a reference set by amplifying by PCR a plurality of samples with a reference nucleic acid sequence together with a signaling agent;
    c) obtaining a time series of signals from every PCR by reading and storing at a plurality of time points at least one signal whose intensity is related to the quantity of the nucleic acid sequence formed in the PCR;
    d) determining the signal in every PCR as a function of the amplification time, wherein the time can also be expressed as a number of reaction cycles;
    e) calculating the first, second or generally the n-th order derivatives of said function, wherein n is an integer;
    f) determining the ordinate maxima of at least two said derivatives as parameters for characterizing the reaction;
    g) simultaneously comparing by a single statistical test the parameters of the investigated PCR with the parameters of the reference set, wherein a parallel geometry indicates reaction kinetics compatible between the investigated PCR and the reference set;
    h) based on the probability obtained by the statistical test, drawing an inference on the geometry of the reaction kinetics of the investigated PCR with those of the PCRs of the reference set; and
    i) informing a user about one or more PCRs with non-parallel geometry if this is elicited in step h.

3. The method of claim 1, wherein at least one parameter is obtained I by smoothing the amplification signal readings with a suitable equation and obtaining values of the equation variables.

4. The method of claim 3, wherein at least one of the parameters describes the slope of the tangent to the smoothing curve at a defined point.

5. The method of claim 1, wherein one of the parameters is the maximal value or mean of plurality of maximal values of the amplification signal.

6. The method of claim 1, wherein at least one parameter is obtained by differentiation or partition of two or more consecutive amplification signal values.

7. The method of claim 1, wherein at least one parameter is the value of the first, second or generally n-derivative at a defined point of the amplification time series of signals.

8. A method for the assessment of compatibility between two or more groups of PCRs with an amplified nucleic acid sequence comprising the steps of:
    a) amplifying by PCR the nucleic acid together with a signaling agent in samples assigned to two or more defined groups;
    b) obtaining a time series of signals from every PCR by reading and storing at a plurality of time points at least one signal whose intensity is related to the quantity of the nucleic acid sequence formed in the PCR;
    c) from the time series of signals of every PCR, deriving a plurality of at least two parameters characterizing change of the signal accompanying the reaction progression;
    d) simultaneously comparing by a single statistical test the parameters between the groups of PCRs;
    e) based on the probability obtained from the statistical test, drawing an inference on the geometry of the reaction kinetics of PCRs between the groups, wherein a parallel geometry indicates reaction kinetics compatible between the groups; and
    f) informing a user about non-parallel geometry of PCRs between the groups if this is elicited in step e.

9. A method for the assessment of compatibility between two or more groups of samples with amplified nucleic acid sequence comprising the steps of:
    a) amplifying by PCR the nucleic acid together with a signaling agent in samples assigned to two or more defined groups;
    b) obtaining a time series of signals from every PCR by reading and storing at a plurality of time points at least one signal whose intensity is related to the quantity of the nucleic acid sequence formed in the PCR;
    c) determining the signal in every PCR as a function of the amplification time, wherein the time can also be expressed as a number of reaction cycles;
    d) calculating the first, second or generally the n-th order derivatives of said function, wherein n is an integer;
    e) determining the ordinate maxima of at least two said derivatives as parameters for characterizing the reaction;
    f) simultaneously comparing by a single statistical test the parameters between the groups of PCRs;
    g) based on the probability obtained from the statistical test, drawing an inference on the geometry of the reaction kinetics of PCRs between the groups, wherein a parallel geometry indicates reaction kinetics compatible between the groups; and
    h) informing a user about non-parallel geometry of PCRs between the groups if this is elicited in step g.

10. The method of claim 9, wherein at least one parameter is obtained by smoothing the amplification signal readings with a suitable equation and obtaining values of the equation variables.

11. The method of claim 10, wherein at least one of the parameters describes the slope of the tangent to the smoothing curve at a defined point.

12. The method of claim 11, wherein one of the parameters is the maximal value or mean of plurality of maximal values of the amplification signal.

13. The method of claim 11, wherein at least one parameter is obtained by differentiation or partition of two or more consecutive amplification signal values.

14. The method of claim 11, wherein at least one parameter is the value of the first, second or generally n-derivative at a defined point of the amplification time series of signals.

* * * * *